(12) United States Patent
Vu et al.

(10) Patent No.: US 9,737,609 B2
(45) Date of Patent: Aug. 22, 2017

(54) NATURAL SUSPENDING AGENT INCLUDING A SYNERGISTIC BLEND OF XANTHAN GUM AND KONJAC POWDER FOR ORAL PHARMACEUTICAL SUSPENSIONS

(71) Applicant: Professional Compounding Centers of America (PCCA), Houston, TX (US)

(72) Inventors: Christine Vu, Richmond, TX (US); Fabiana Banov, Sugar Land, TX (US); Daniel Banov, Sugar Land, TX (US)

(73) Assignee: Professional Compounding Centers of America (PCCA), Houston, TX (US)

( * ) Notice: Subject to any disclaimer, the term of this patent is extended or adjusted under 35 U.S.C. 154(b) by 0 days.

(21) Appl. No.: 14/830,500

(22) Filed: Aug. 19, 2015

(65) Prior Publication Data

US 2016/0051684 A1   Feb. 25, 2016

Related U.S. Application Data

(60) Provisional application No. 62/039,771, filed on Aug. 20, 2014.

(51) Int. Cl.
*A61K 47/36* (2006.01)
*A61K 47/22* (2006.01)
(Continued)

(52) U.S. Cl.
CPC ............ *A61K 47/36* (2013.01); *A61K 9/0095* (2013.01); *A61K 31/4439* (2013.01);
(Continued)

(58) Field of Classification Search
None
See application file for complete search history.

(56) References Cited

U.S. PATENT DOCUMENTS

2002/0019447 A1   2/2002   Renn et al.
2004/0131645 A1   7/2004   Williams et al.
(Continued)

FOREIGN PATENT DOCUMENTS

CA         2039566       10/1991
WO    2013142482 A1      9/2013
(Continued)

*Primary Examiner* — Jianfeng Song
(74) *Attorney, Agent, or Firm* — David G. Woodral; Scott R. Zingerman; Gable Gotwals

(57) ABSTRACT

The present disclosure refers to a synergistic blend of Konjac powder and Xanthan gum that is included, as a natural suspending agent, in oral pharmaceutical suspensions. Oral pharmaceutical suspensions comprising the synergistic blend are aqueous solutions. The synergistic blend, used as a suspension agent to suspend suitable active pharmaceutical ingredients (APIs), improves the stability of oral pharmaceutical suspensions, and helps in the formation of a thermo-reversible gel and shear thinning necessary to keep APIs suspended within oral pharmaceutical suspensions. The synergistic blend of Konjac powder and Xanthan gum has unique anti-flocculation properties, which improve the homogeneity of the oral pharmaceutical suspensions. Additionally, the blend provides a better texture and mouth feel. Oral pharmaceutical suspensions, comprising the synergistic blend, include a vehicle, such as water, as well as different components, such as, for example APIs, preservatives, sweeteners, flavoring agents, and pH regulators or buffers, among others.

17 Claims, 2 Drawing Sheets

(51) Int. Cl.
*A61K 47/18* (2017.01)
*A61K 47/46* (2006.01)
*A61K 31/575* (2006.01)
*A61K 31/4439* (2006.01)
*A61K 47/12* (2006.01)
*A61K 9/00* (2006.01)
*A61K 47/26* (2006.01)

(52) U.S. Cl.
CPC ............ *A61K 31/575* (2013.01); *A61K 47/12* (2013.01); *A61K 47/26* (2013.01); *A61K 47/183* (2013.01); *A61K 47/46* (2013.01)

(56) References Cited

U.S. PATENT DOCUMENTS

| | | | | |
|---|---|---|---|---|
| 2009/0093448 | A1* | 4/2009 | Pfaff | C07J 31/006 514/177 |
| 2010/0048451 | A1* | 2/2010 | Asotra | A61K 9/06 514/1.1 |
| 2010/0069323 | A1* | 3/2010 | Seto | A61K 9/0014 514/54 |
| 2012/0201952 | A1* | 8/2012 | Catani | A23L 1/236 426/658 |

FOREIGN PATENT DOCUMENTS

| | | |
|---|---|---|
| WO | 2014047731 A1 | 4/2014 |
| WO | 2014/089174 A1 | 6/2014 |
| WO | PCT/US2015/046026 | 12/2015 |

\* cited by examiner

100

102

104

106

NATURAL SUSPENDING AGENT INCLUDING A SYNERGISTIC BLEND OF XANTHAN GUM AND KONJAC POWDER FOR ORAL PHARMACEUTICAL SUSPENSIONS

CROSS-REFERENCE TO RELATED APPLICATIONS

This application claims the benefit of U.S. Provisional Application Ser. No. 62/039,771, filed Aug. 20, 2014, which is hereby incorporated by reference.

BACKGROUND

Field of the Disclosure

The present disclosure relates generally to pharmaceutical compositions, and more particularly, to natural suspending agents that improve stability in oral pharmaceutical suspensions.

Background Information

Some drugs are insoluble in all acceptable media and must, therefore, be administered as a tablet, capsule, or as a suspension. In some situations, suspensions possess certain advantages over other dosage forms. Because of their liquid character, suspensions represent an ideal dosage form for patients who have difficulty swallowing tablets or capsules. This factor is of particular importance in the administration of drugs to children and elderly persons. Additionally, suspensions of insoluble drugs can also be used externally, often as protective agents.

One challenge of suspension formulation is sedimentation, caking, distribution, and re-suspension of the solid particles. A suspension should not settle rapidly and it should be sufficiently fluid to flow easily under the conditions of administration. Because suspensions are energetically unstable, the particles that have settled tend to interact to form a cake or hard crystalline network. To prevent this, suspensions are formulated such that caking is minimized so particles that have settled can be readily re-dispersed upon shaking.

Pharmaceutical suspensions consist of solid particles of variable sizes dispersed in a liquid medium, generally an aqueous solution. Typically, pharmaceutical suspensions include a suspending agent that helps the active pharmaceutical ingredients (APIs) stay suspended in the liquid medium, thereby reducing caking at the bottom of the suspension. Consistency of the solid particles throughout the suspending medium is facilitated with the API as solid particles staying suspended in the continuous phase, thereby allowing consistent withdrawal of uniform doses. One of the properties of a well-formulated suspension is that it should easily be re-suspended by the use of moderate agitation. A good suspension should allow the withdrawal of uniform and accurate doses throughout the period of medication.

Konjac glucomannan powder, which may be used as a suspending agent, is a pure natural, odorless soluble fiber that is produced from the Konjac plant. Konjac powder does not include protein, fat, sugar or starch. Konjac powder is also gluten free and wheat free, and does not have any calories. Konjac powder can be used as a thickening agent in many applications, such as, for example in food, drinks, pharmaceuticals, cosmetics, and the like. It has about ten times the thickening power of cornstarch. Additionally, Konjac powder does not thicken very much when mixed with cold water, but quickly thickens when it is heated.

Xanthan gum is widely used in cosmetics and personal care industry as a rheology control agent for aqueous systems. However, currently available Xanthan gum needs to be improved to enhance its properties, broaden its applications, and provide functionality at a lower cost.

Oral dosage forms have stability problems associated with maintaining the APIs in suspension. Stability problems include sedimentation, creaming, crystal growth (agglomeration), separation and difficulty to re-disperse to obtain original suspensions. Many oral pharmaceutical suspensions enable the APIs to settle out as sediment or creaming to the surface, thereby having variations in the therapeutic concentration of APIs within the suspension. This results in under dosing or over dosing of the patient, which may seriously compromise the patient's recovery.

Additionally, oral pharmaceutical suspensions should be readily pourable so that the dose is easy to administer. The requirement that oral pharmaceutical suspensions be readily pourable effectively places an upper limit on the viscosity of the suspensions. This restriction also limits the amount of APIs that the overall composition will suspend. Moreover, it has been shown that the type of suspending agents rather than the physical characteristics of the APIs appear to have the main influence on the physical stability of suspensions.

SUMMARY

The present disclosure refers to a synergistic blend of Konjac powder and Xanthan gum that is included, as a natural suspending agent, in oral pharmaceutical suspensions. Further, oral pharmaceutical suspensions including the synergistic blend of Konjac powder and Xanthan gum are aqueous solutions that may include natural sweeteners, such as Monk fruit sweetener, among other suitable ingredients.

In some embodiments, the synergistic blend of Konjac powder and Xanthan gum is used as a suspension agent to suspend suitable active pharmaceutical ingredients (APIs), thereby improving the stability of oral pharmaceutical suspensions.

In some embodiments, the synergistic blend of Konjac powder and Xantham gum produces a synergistic polymer complex that provides a unique thixotropic flow (e.g., it thins as it is shaken and thickens upon standing). In these embodiments, the synergistic blend enables a rapid redispersion of APIs with agitation and minimizes sedimentation. The synergistic effect of the blend of Konjac powder and Xanthan gum is due to the intermolecular binding, which involves co-crystallization of sections of the disordered Xanthan chain with the structurally similar segments of the Konjac Mannan.

In some embodiments, the synergistic blend of Konjac powder and Xanthan gum enables the formation of a thermo-reversible gel and shear thinning. In these embodiments, the synergistic blend of Konjac powder and Xanthan gum has improved anti-flocculation properties that help in the homogeneity of the oral pharmaceutical suspensions. Further to these embodiments, the synergistic blend of Konjac powder and Xanthan gum provides a better texture and mouth feel.

In some embodiments, the oral pharmaceutical suspensions, comprising the synergistic blend of Konjac powder and Xanthan gum, additionally include suitable vehicles, such as water, as well as different components, such as APIs, preservatives, natural sweeteners, flavoring agents, and pH regulators or buffers, among others. In these embodiments, the oral pharmaceutical suspensions are organoleptically pleasing.

In some embodiments, the oral pharmaceutical suspensions, comprising the synergistic blend of Konjac powder and Xanthan gum, include one or more APIs. In these embodiments, the oral pharmaceutical suspensions are employed to treat a patient in need of a therapeutically effective amount of a specific API or APIs.

In some embodiments, the synergistic blend of Konjac powder with Xanthan gum enables APIs to remain suspended with agitation (e.g., stirring or shaking). In these embodiments, the synergistic blend decreases the sedimentation velocity of the dispersed APIs by maintaining the viscosity of the suspension at a constant level, minimizing or delaying the formation of precipitates to distribute the APIs homogeneously in the whole suspension during the period of circulation. Thus, when the pharmaceutical suspension is administered to patients, the viscosity of the synergistic blend guarantees an intake of a pre-determined amount of API. The sedimentation velocity decreases as the suspension's viscosity increases, but a high viscosity makes intake difficult for patients to tolerate. Further to these embodiments, the synergistic blend is hydrated in an aqueous solution to exhibit viscosity, or floats in an aqueous solution without sinking rapidly, thereby delaying the sedimentation of the APIs. A rapid reduction of viscosity occurs when shaking or stirring is applied to the suspension (shear thinning), thereby improving the uniformity of the suspension as well as making the suspension more suitable for patient intake. Because Konjac powder is a soluble fiber, and has known health benefits, the synergy exhibited between Xanthan gum and Konjac powder does not only provide a stable suspending vehicle, but also provides health benefits as a soluble fiber.

In an example, the synergistic blend of Konjac powder and Xanthan gum is used to make oral pharmaceutical suspensions which includes: from about 40% w/w to 99.5% w/w of water; from about 0.1% w/w to 0.3% w/w of Konjac powder; from about 0.01% w/w to 0.1% w/w of Xanthan gum; from about 0.2% w/w to 1% w/w of suitable preservatives, such as sodium benzoate and/or potassium sorbate, or the like; from about 0.1% w/w to 0.5% w/w of Monk fruit sweetener; and from about 0.1% w/w to 1% w/w of a pH regulator agent, such as gluconolactone, citric acid, or the like.

In some embodiments, the synergistic blend of Konjac powder and Xanthan gum provides oral pharmaceutical suspensions with pH from about 4.0 to about 6.0, more preferably from about 5.0 to about 6.0, and most preferably from about 5.3 to about 6.0.

In some embodiments, the oral pharmaceutical suspensions including the synergistic blend of Konjac powder and Xanthan gum can be administered in suitable doses as directed by a physician. In other embodiments, the synergistic blend of Konjac powder and Xanthan gum is used to make oral pharmaceutical suspensions for veterinary use.

In other embodiments, polymers that can be used as natural suspending agents in oral pharmaceutical suspensions include acacia, agar, carrageenan guar, inulin, pectin, tara gum, pullulan, tragacanth, karaya, carboxylmethylcellulose, arabic, cassia, guar gum, chatti, locust bean gum, hydroxyethylcellulose gum, hyaluronic acid, and mixture thereof, among others.

Numerous other aspects, features, and benefits of the present disclosure may be made apparent from the following detailed description.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Definitions

Figure 1:
FIG. 1 is a graphical representation illustrating results of a physical stability test performed on three (3) oral pharmaceutical suspensions including spironolactone in a concentration of about 5 mg/mL, stored at room temperature without shaking, according to an embodiment.
Figure 1:
Figure 1:
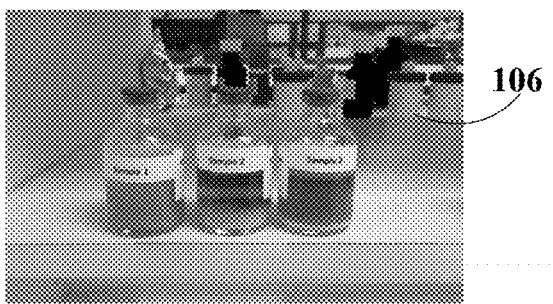

As used here, the following terms have the following definitions:

"Active Pharmaceutical Ingredients (APIs)" refer to chemical compounds that induce a desired effect, and include agents that are therapeutically effective, prophylactically effective, or cosmeceutically effective.

"Patient" refers to warm-blooded animals, such as mammals, for example, humans, who are in need of treatment.

"Stability" refers to the chemical and physical integrity of the dosage unit and, when appropriate, the ability of the dosage unit to maintain protection against microbiological contamination.

"Suspension" refers to a coarse dispersion in which insoluble solid particles are suspended in a liquid medium.

"Suspending agent" refers to a substance that helps an API or APIs stay in the body of a suspension, thereby preventing caking at the bottom.

"Therapeutically effective amount" refers to the amount of subject compound that will elicit the biological or medical response of a tissue, system, animal or human that is being sought.

"Thixotropic flow" refers to a reversible, time dependent, isothermal gel-sol transition, in which certain gels or fluids that are thick (viscous) under static conditions will flow (become thin, less viscous) over time when shaken, agitated, or otherwise stressed.

"Vehicle" refers to carrier materials suitable for pharmaceutical formulations.

Description of the Disclosure

The present disclosure refers to a synergistic blend of Konjac powder and Xanthan gum that is included, as a natural suspending agent, in oral pharmaceutical suspensions. Further, oral pharmaceutical suspensions including the synergistic blend of Konjac powder and Xanthan gum are aqueous solutions that may include natural sweeteners, such as Monk fruit sweetener, among other suitable ingredients.

In some embodiments, the synergistic blend of Konjac powder and Xanthan gum is used as a suspension agent to suspend suitable active pharmaceutical ingredients (APIs), thereby improving the stability of oral pharmaceutical suspensions.

In some embodiments, the synergistic blend of Konjac powder and Xantham gum produces a synergistic polymer complex that provides a unique thixotropic flow (e.g., it thins as it is shaken and thickens upon standing). In these embodiments, the synergistic blend enables a rapid redispersion of APIs with agitation and minimizes sedimentation.

The synergistic interaction between Konjac powder and Xanthan gum occurs by the attachment of segments of Konjac to the cellulose backbone of disordered Xanthan segments, rather than to the Xanthan helix. This is supported by two facts: (i) the appearance of new X-ray fiber patterns assigned to the binding between Xanthan gum and Konjac powder for oriented mixed gels, and (ii) the suppression of gelation for mixing under conditions where Xanthan is in the helix conformation. The interacting site of Glucomannans has been confirmed by observation of the synergistic gelation of galactose-depleted Xanthan, to be composed of consecutive unsubstituted Mannan segments.

In some embodiments, the synergistic blend of Konjac powder and Xanthan gum enables the formation of a thermo-reversible gel and shear thinning. In these embodiments, the synergistic blend of Konjac powder and Xanthan gum has improved anti-flocculation properties that help in the homogeneity of the oral pharmaceutical suspensions. Further to these embodiments, the synergistic blend of Konjac powder and Xanthan gum provides a better texture and mouth feel.

Sedimentation of particles in a suspension is governed by several factors, such as, for example particle size, density of the particles, density of the vehicle, and viscosity of the vehicle, among others. The velocity of sedimentation of particles in a suspension can be determined by using the conventional Stoke's equation. According to the Stoke's equation, the velocity of sedimentation of particles in a suspension can be reduced by decreasing the particle size and also by minimizing the difference between the densities of the particles and the vehicle. Because the density of the particles is constant for a particular substance and cannot be changed, the changing of the density of the vehicle close to the density of the particle might minimize the difference between the densities of the particles and the vehicle. The velocity of sedimentation can also be affected by the viscosity of the vehicle. The velocity of sedimentation decreases as the viscosity of the vehicle increases. The viscosity and density of any vehicle are related to each other, so any attempt to change one of these parameters can also change the other one.

Because sedimentation of particles cannot be completely avoided, it is desirable that the particles should settle slowly. The formulation should enable the easy re-dispersion of sedimented particles in a suspension for the uniformity of dose. Thus, a flocculated suspension is desirable than a de-flocculated suspension. It is also desirable that a suspension should not be too viscous to reduce the sedimentation rate. A highly viscous suspension would make pouring difficult. A well-formulated suspension should pour readily and evenly. Sedimentation behavior of oral suspensions depends largely on the motion of the particles which is thermally or gravitationally induced. If a suspended particle is sufficiently small in size, the thermal forces dominate the gravitational forces and the particle follows a random motion owing to molecular bombardment, called Brownian motion.

In some embodiments, the oral pharmaceutical suspensions, comprising the synergistic blend of Konjac powder and Xanthan gum, include one or more APIs, such as antibiotics and antifungal agents. In these embodiments, the oral pharmaceutical suspensions are used to treat a patient in need of a therapeutically effective amount of a specific API or APIs. Further to these embodiments, the oral pharmaceutical suspensions have a homogeneity that enables the APIs to be uniformly dispersed but undissolved within the vehicle.

In some embodiments, the oral pharmaceutical suspensions, comprising the synergistic blend of Konjac powder and Xanthan gum, additionally include suitable ingredients, such as, for example excipients, surface active agents, dispersing agents, sweetening agents, flavoring agents, coloring agents, preservatives, oily vehicles, solvents, suspending agents, dispersing agents, emulsifying agents, pH regulator agents, buffers, salts, antioxidants, and stabilizing agents, among others. In these embodiments, the oral pharmaceutical suspensions are organoleptically pleasing.

Thickening agents are pharmaceutically acceptable excipients that add a desired viscosity and flow to a formulation, such as an oral suspension. The synergistic blend of Konjac powder and Xanthan gum is suitable thickening, or gelling agent, thereby providing good sensory appeal and texture. The rheology of the synergistic blend provides for a high yield value, low shear thinning quality, in non-thixotropic liquid formulations, such as in oral pharmaceutical suspensions.

In some embodiments, a buffer can be used to provide an oral pharmaceutical suspension that enables a soft mouth feel, by maintaining the suspension's pH at a constant level during the period of circulation, and providing appropriate acidity to the oral pharmaceutical suspension. In these embodiments, buffers include citric acid, gluconolactone, sodium citrate, tartaric acid and salts thereof, fumaric acid, sodium acetate, and the like.

A preservative can be used to prevent the chemical deterioration of products during the period of circulation. In some embodiments, the preservative can be selected freely from pharmaceutically acceptable conventional preservatives. Preferably, the preservative can be selected from sodium benzoate and potassium sorbate. In other embodiments, the preservative is selected from benzoic acid, methyl paraoxybenzoate, ethyl paraoxybenzoate, (iso)propyl paraoxybenzoate, (iso)butyl paraoxybenzoate, sorbic acid, sodium sorbate, dehydroacetic acid, sodium dehydroacetate, chbrobutanol, benzalkonium chloride, benzenthonium chbride, phenol (p type), cresol, chbrocresol, benzyl alcohol, or the like.

In some embodiments, the oral pharmaceutical suspensions also include Edetate Disodium (EDTA). EDTA is a chelating agent that forms a stable water-soluble complex with alkaline earth and heavy metal ions. EDTA is useful as an antioxidant synergist, sequestering metal ions that might otherwise catalyze autoxidation reactions. EDTA also has synergistic effects as an antimicrobial when used in combination with other preservatives.

The sweetener and flavor can be used to improve the administration compliance by providing a good taste. In some embodiments, the sweetener can be selected freely from acceptable natural sweeteners. Preferably, the sweetener is Monk fruit sweetener. In other embodiments, sweeteners are selected from sucrose, fructose, honey, sodium saccharin, cydamate, aspartame, xylitol, erythritol, and acesulfame, among others. In further embodiments, the flavor is selected freely from pharmaceutically acceptable conventional flavors. Preferably, lemon lime flavor, lemon essence, strawberry flavor, banana flavor, chocolate flavor, milk flavor, or the like, is used.

The Monk fruit is a small sweet melon native to China and Southeast Asia. Legend has it that Buddhist monks cultivated the lemon-sized fruit in the 13th century. In China its known as luo han guo and has traditionally been used in herbal medicine. Now Monk fruit-derived sweeteners have entered the Western market, where they are touted for having zero carbohydrates and low or no calories.

Monk fruit sweeteners, such as Monk fruit in the raw and nectresse are made from Monk fruit extract, which is 200 to 300 times sweeter than sugar. The consistency of Monk fruit sweetener is similar to granulated sugar and is heat stable.

In some embodiments, the oral pharmaceutical suspensions, comprising the synergistic blend of Konjac powder and Xanthan gum, include an anti-foaming agent to increase convenience in production and administration of the oral pharmaceutical suspensions by suppressing the generation of bubbles when the oral pharmaceutical suspensions are shaken in formulation and administration. In these embodiments, the anti-foaming agent can be selected freely from pharmaceutically acceptable conventional anti-foaming agents, such as, for example simethicone, simethicone emulsion, methyl oleate, glyceryl oleate, sorbitan laurate, sorbitan oleate, or the like.

In some embodiments, the synergistic blend of Konjac powder with Xanthan gum enables APIs to remain suspended with agitation (e.g., stirring or shaking). In these embodiments, the synergistic blend decreases the sedimentation velocity of the dispersed APIs by maintaining the viscosity of the suspension at a constant level, minimizing or delaying the formation of precipitates to distribute the APIs homogeneously in the whole suspension during the period of circulation. Thus, when the pharmaceutical suspension is administered to patients, the viscosity of the synergistic blend guarantees an intake of a pre-determined amount of API. The sedimentation velocity decreases as the suspension's viscosity increases, but a high viscosity makes intake difficult for patients to tolerate. Further to these embodiments, the synergistic blend is hydrated in an aqueous solution to exhibit viscosity, or floats in an aqueous solution without sinking rapidly, thereby delaying the sedimentation of the APIs. A rapid reduction of viscosity occurs when shaking or stirring is applied to the suspension (shear thinning), thereby improving the uniformity of the suspension as well as making the suspension more suitable for patient intake. Because Konjac powder is a soluble fiber, and has known health benefits, the synergy exhibited between Xanthan gum and Konjac powder does not only provide a stable suspending vehicle, but also provides health benefits as a soluble fiber.

In an example, the synergistic blend of Konjac powder and Xanthan gum is used to make oral pharmaceutical suspensions which includes: from about 40% w/w to 85% w/w of water; from about 0.1% w/w to 0.3% w/w of Konjac powder; from about 0.01% w/w to 0.1% w/w of Xanthan gum; from about 0.2% w/w to 1% w/w of suitable preservatives, such as sodium benzoate and/or potassium sorbate, or the like; from about 0.1% w/w to 0.5% w/w of Monk fruit sweetener; and from about 0.1% w/w to 1% w/w of a pH regulator agent, such as gluconolactone, citric acid, or the like.

In some embodiments, the synergistic blend of Konjac powder and Xanthan gum provides oral pharmaceutical suspensions with pH from about 4.0 to 6.0, more preferably from about 5.0 to 6.0, and most preferably from about 5.3 to 6.0.

In some embodiments, the oral pharmaceutical suspensions including the synergistic blend of Konjac powder and Xanthan gum can be administered in suitable doses as directed by a physician. In other embodiments, the synergistic blend of Konjac powder and Xanthan gum is used to make oral pharmaceutical suspensions for veterinary use.

In other embodiments, polymers that can be used as natural suspending agents in oral pharmaceutical suspensions include acacia, agar, carrageenan guar, inulin, pectin, tara gum, pullulan, tragacanth, karaya, carboxylmethylcellulose, arabic, cassia, guar gum, chatti, locust bean gum, hydroxyethylcellulose gum, hyaluronic acid, and mixture thereof, among others.

Tests

Evaluation of the Content Uniformity of Oral Pharmaceutical Suspensions Including the Synergistic Blend of Konjac Powder and Xanthan Gum This study was conducted to evaluate the content uniformity of nine (9) oral pharmaceutical suspensions including the synergistic blend of Konjac powder and Xantham gum.

Methodology: The evaluation of the content uniformity of the nine oral pharmaceutical suspensions was divided in three (3) stages: (1) elaboration of the suspensions; (2) preparation of the unit dose oral syringes; and (3) High-Performance Liquid Chromatography (HPLC) assay.

(1) Elaboration of the suspensions: The nine suspensions were elaborated (compounded) in accordance with the Standard Operating Procedures (SOPs) indicated in the respective PCCA Formulas (Table 1). Each oral pharmaceutical suspension included one API dispersed in an oral pharmaceutical suspension base formulation including the synergistic blend of Konjac powder and Xantham gum in a total volume of 150 mL (APIs and dosage strengths are illustrated in Table 1).

(2) Preparation of the unit dose oral syringes: For each oral pharmaceutical suspension, the total volume of 150 mL was divided in 30 unit dose oral syringes of 5 mL each; suspensions were shaken prior to the drawing of each unit dose. In accordance with the United States Pharmacopeia (USP) General Chapter <905> "Uniformity of Dosage Units", a random sample of 10 unit dose oral syringes was selected and tested individually for each oral pharmaceutical suspension, using an appropriate analytical method for chemical characterization.

(3) HPLC assay: The content of uniformity of the nine oral pharmaceutical suspensions was measured by reverse phase HPLC. The chromatographic system (Waters 2695, Alliance) used a reversed phase C18 column (Xbridge C18, 4.6×150 mm, 5 um, Waters), which was maintained at 40° C. The mobile phase was composed of acetonitrile, or methanol, and water acidified with formic acid 0.1%, in selected ratios depending on the API analysis. The injection volume was 10 µL and the flow rate was maintained at 0.8 to 1 mL/min Each sample was injected twice. The chromatographic system was equipped with a Photodiode Array (PDA) detector (Waters 2998, Alliance) and detection was carried out at variable wavelength according to the maximum absorption of each API. The data acquisition software was Empower 3 feature release 2.

Results and Discussion: The content uniformity is determined by calculating the Acceptance Value (AV), which is the limit that the observed mean potency is allowed to deviate from the label claim. In accordance to the USP General Chapter <905> "Uniformity of Dosage Units," the requirements for dosage uniformity are met if the AV of the 10 unit doses is ≤15%. If the AV is >15%, 20 additional unit doses must be tested and the AV recalculated. The AV for all nine oral pharmaceutical suspensions was <15% (Table 1) and, therefore, the requirements for dosage uniformity were met and there was no need for additional testing. The test for content uniformity demonstrated the consistency of unit doses for all nine oral pharmaceutical suspensions. In practice, if 5 mL of omeprazole 2 mg/mL in oral pharmaceutical suspensions were to be administered to a patient, since each unit dose has an API content within a narrow range around the label claim, the patient would consistently receive approximately 10 mg of omeprazole.

Conclusions: This study has demonstrated that all nine oral pharmaceutical suspensions were uniform in content. By following the SOPs set forth in the PCCA formulas (Table 1), compounding pharmacists are thus likely to meet the requirements of content uniformity and, as a result, dispense unit dose oral syringes in accordance to the label claim.

TABLE 1

PCCA formula number and chemical characterization of nine oral pharmaceutical suspensions.

| Oral Pharmaceutical Suspension | PCCA Formula | Mean Potency (%) | Acceptance Value (%) |
|---|---|---|---|
| Omeprazole 2 mg/mL | 11262 | 91.51 | 14.90 |
| Captopril 5 mg/mL | 11201 | 102.63 | 5.15 |
| Enalapril Maleate 0.5 mg/mL | 11200 | 106.23 | 7.46 |
| Hydrochlorothiazide 10 mg/mL | 11202 | 106.18 | 8.59 |
| Metronidazole 50 mg/mL | 11203 | 108.53 | 9.69 |
| Nystatin 100,000 Units/mL | 11204 | 100.06 | 3.25 |
| Rifampin 10 mg/mL | 11206 | 103.08 | 3.66 |
| Spironolactone 5 mg/mL | 11207 | 103.18 | 3.92 |
| Vancomycin HCl 50 mg/mL | 11209 | 92.72 | 9.21 |

Evaluation of the Physical Stability of Oral Pharmaceutical Suspensions Including the Synergistic Blend of Konjac Powder and Xanthan Gum This study was conducted to evaluate the physical stability of six (6) oral pharmaceutical suspensions including the synergistic blend of Konjac powder and Xantham gum.

Methodology: For this study, three (3) different oral pharmaceutical suspension base formulations were elaborated (compounded) as illustrated in Table 2. Further, six (6) different oral pharmaceutical suspensions were compounded as follows: a) three (3) oral pharmaceutical suspensions including spironolactone in a concentration of about 5 mg/mL, and b) three (3) oral pharmaceutical suspensions including metronidazole benzoate in a concentration of about 50 mg/mL.

TABLE 2

Oral pharmaceutical suspension base formulations.

| Ingredient | TC 178.54 | TC 178.47 | TC 178.48 |
|---|---|---|---|
| Water | 98.8323 | 98.25 | 98.10 |
| Sodium Benzoate | 0.40 | 0.80 | 0.80 |
| Gluconolactone | — | 0.50 | 0.50 |
| Purefruit Select (Monk Fruit Extract) | 0.20 | 0.20 | 0.20 |
| Konjac Powder (Konjac Glucomannan) | 0.20 | — | 0.20 |
| Potassium Sorbate | 0.30 | 0.20 | 0.20 |
| Xanthan Gum | 0.05 | 0.05 | — |
| Citric Acid | 0.0177 | — | — |
| Total | 100.00 | 100.00 | 100.00 |

Results and Discussion: The results of the physical stability test performed on the six (6) oral pharmaceutical suspensions are illustrated in FIGS. 1 and 2.

Figure 2:
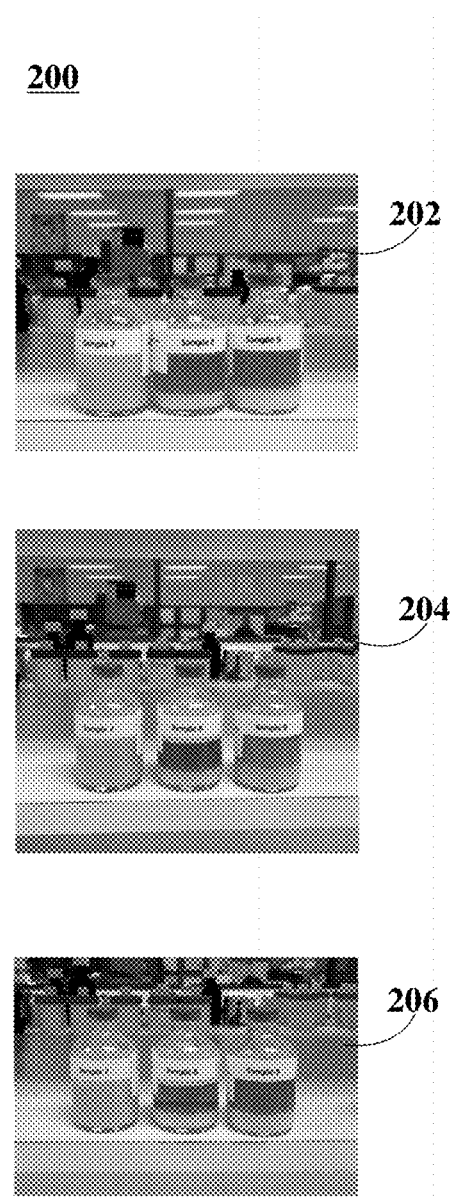
FIG. 2 is a graphical representation illustrating results of a physical stability test performed on three (3) oral pharmaceutical suspensions including metronidazole benzoate in a concentration of about 50 mg/mL, stored at room temperature without shaking, according to an embodiment.

FIG. 1 is a graphical representation illustrating results of a physical stability test performed on three (3) oral pharmaceutical suspensions including spironolactone in a concentration of about 5 mg/mL, stored at room temperature without shaking, according to an embodiment. In FIG. 1, physical stability test 100 includes sample set 102, sample set 104, and sample set 106. Further, sample sets include sample 1 (base TC 178.54), sample 2 (base TC 178.47), and sample 3 (TC 178.48).

In this study, sample set 102 illustrates test results for oral pharmaceutical suspensions immediately after being elaborated. Sample set 104 illustrates test results for oral pharmaceutical suspensions at about 1 hour post-preparation. Sample set 106 illustrates test results for oral pharmaceutical suspensions at about 72 hours post-preparation.

In FIG. 1, oral pharmaceutical suspension within sample #1 maintained homogeneity even when stored at room temperature and without shaking at about 72 hours post-preparation (sample set 106). Therefore, the synergistic blend of Konjac powder and Xanthan gum is proven by the uniformly distributed dispersed phase obtained. The synergistic blend of Konjac powder and Xanthan gum decreased the sedimentation velocity of the dispersed spironolactone by maintaining the viscosity of the oral pharmaceutical suspension at a constant level, minimizing or delaying the formation of precipitates to distribute the spironolactone homogeneously within the whole oral pharmaceutical suspension during the period of study.

FIG. 2 is a graphical representation illustrating results of a physical stability test performed on three (3) oral pharmaceutical suspensions including metronidazole benzoate in a concentration of about 50 mg/mL, stored at room temperature without shaking, according to an embodiment. In FIG. 2, physical stability test 200 includes sample set 202, sample set 204, and sample set 206. Further, sample sets include sample 7 (base TC 178.54), sample 8 (base TC 178.47), and sample 9 (TC 178.48).

In this study, sample set 202 illustrates test results for oral pharmaceutical suspensions immediately after being elaborated. Sample set 204 illustrates test results for oral pharmaceutical suspensions at about 1 hour post-preparation. Sample set 206 illustrates test results for oral pharmaceutical suspensions at about 72 hours post-preparation.

In FIG. 2, oral pharmaceutical suspension within sample #7 maintained homogeneity even when stored at room temperature and without shaking at about 72 hours post-preparation (sample set 206). Therefore, the synergistic blend of Konjac powder and Xanthan gum is proven by the uniformly distributed dispersed phase obtained. The synergistic blend of Konjac powder and Xanthan gum decreased the sedimentation velocity of the dispersed metronidazole benzoate by maintaining the viscosity of the oral pharmaceutical suspension at a constant level, minimizing or delaying the formation of precipitates to distribute the metronidazole benzoate homogeneously within the whole oral pharmaceutical suspension during the period of study.

Conclusions: This study has demonstrated that all six oral pharmaceutical suspensions were homogeneous and stable, even when stored at room temperature and without shaking at about 72 hours post-preparation.

The following examples are intended to illustrate the scope of the disclosure and are not intended to be limiting. It is to be understood that other pharmaceutical formulations known to those skilled in the art may alternatively be used.

EXAMPLES

Formulation examples of the oral pharmaceutical suspensions are described below.

Example #1 illustrates formula for ursodiol 60 mg/mL oral suspension:

| Ingredient | Composition |
| --- | --- |
| Ursodiol USP | 6 g |
| Acesulfame potassium FCC | 0.5 g |
| Steviol glycosides 95% | 0.5 g |
| Flavor (artificial), raspberry | 3 mL |
| Flavor (artificial), marshmallow | 1 mL |
| Disclosed suspension base | q.s. 100 mL |

Example #2 illustrates formula for lansoprazole 3 mg/mL oral suspension:

| Ingredient | Composition |
| --- | --- |
| Lansoprazole USP | 0.3 g |
| Acesulfame potassium FCC | 0.3 g |
| Steviol glycosides 95% | 0.3 g |
| Sodium bicarbonate USP | 11 g |
| Polysorbate 20 NF | 0.2 mL |
| Flavor (artificial), watermelon | 4 mL |
| Sodium hydroxide 10% (w/v) aqueous solution | To adjust pH |
| Disclosed suspension base | q.s. 100 mL |

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

What is claimed is:

1. A pharmaceutical composition comprising an oral suspension comprising water, konjac glucomannan powder, and xanthan gum uniformly dispersed in the oral suspension in a ratio that forms a thixotropic solution, and at least one active pharmaceutical ingredient wherein the pharmaceutical composition comprises about 0.1% w/w to about 0.3% w/w konjac glucomannan powder and about 0.01% w/w to 0.05 w/w xanthan gum.

2. The pharmaceutical composition of claim 1, wherein the pharmaceutical composition further comprises monk fruit sweetener.

3. The pharmaceutical composition of claim 1, wherein the pharmaceutical composition further comprises at least one preservative.

4. The pharmaceutical composition of claim 3, wherein the at least one preservative includes at least one selected from the group consisting of sodium benzoate and potassium sorbate.

5. The pharmaceutical composition of claim 3, wherein the pharmaceutical composition further comprises at least one pH regulator.

6. The pharmaceutical composition of claim 5, wherein the pH of the pharmaceutical composition is about 4 to about 6.

7. The pharmaceutical composition of claim 6, wherein the pH of the pharmaceutical composition is about 5 to about 6.

8. The pharmaceutical composition of claim 7, wherein the pH of the pharmaceutical composition is about 5.3 to about 6.

9. The pharmaceutical composition of claim 5, wherein the at least one pH regulator includes at least one selected from the group consisting of citric acid, gluconolactone, sodium citrate, tartaric acid and salts thereof, fumaric acid, and sodium acetate.

10. The pharmaceutical composition of claim 9, wherein the at least one pH regulator includes gluconolactone.

11. The pharmaceutical composition of claim 1, wherein the pharmaceutical composition further comprises about 0.1% w/w to about 0.5% w/w of monk fruit sweetener.

12. The pharmaceutical composition of claim 1, wherein the pharmaceutical composition further comprises about 0.1% w/w to about 1% w/w of at least one pH regulator.

13. The pharmaceutical composition of claim 12, wherein the pharmaceutical composition further comprises about 0.2% w/w to about 1% w/w of at least one preservative.

14. The pharmaceutical composition of claim 3, wherein the at least one preservative includes at least one selected from the group consisting of benzoic acid, methyl paraoxybenzoate, ethyl paraoxybenzoate, (iso)propyl paraoxybenzoate, (iso)butyl paraoxybenzoate, sorbic acid, sodium sorbate, dehydroacetic acid, sodium dehydroacetate, chlorobutanol, benzalkonium chloride, benzenthonium chloride, phenol (p type), cresol, chlorocresol, and benzyl alcohol.

15. The pharmaceutical composition of claim 5, wherein the pharmaceutical composition further comprises at least one natural suspension agent selected from the group consisting of acacia, agar, carrageenan guar, inulin, pectin, tara gum, pullulan, tragacanth, karaya, carboxylmethylcellulose, arabic, cassia, guar gum, chatti, locust bean gum, hydroxyethylcellulose gum, and hyaluronic acid.

16. The pharmaceutical composition of claim 5, wherein the pharmaceutical composition further comprises at least one chelating agent.

17. The pharmaceutical composition of claim 16, wherein the at least one chelating agent comprises edetate disodium.

\* \* \* \* \*